(12) United States Patent
Augusto

(10) Patent No.: US 10,001,427 B2
(45) Date of Patent: Jun. 19, 2018

(54) LEAK DETECTOR

(71) Applicant: Universal Enterprises, Inc., Beaverton, OR (US)

(72) Inventor: David W. Augusto, Micco, FL (US)

(73) Assignee: Kane USA, Inc., Beaverton, OR (US)

( * ) Notice: Subject to any disclaimer, the term of this patent is extended or adjusted under 35 U.S.C. 154(b) by 324 days.

(21) Appl. No.: 15/044,069

(22) Filed: Feb. 15, 2016

(65) Prior Publication Data
US 2017/0234761 A1    Aug. 17, 2017

(51) Int. Cl.
*G01N 21/3504*    (2014.01)
*G01M 3/38*    (2006.01)

(52) U.S. Cl.
CPC .......... *G01M 3/38* (2013.01); *G01N 21/3504* (2013.01)

(58) Field of Classification Search
CPC ................................................ G01N 21/3504
See application file for complete search history.

(56) References Cited

U.S. PATENT DOCUMENTS

| | | | | |
|---|---|---|---|---|
| 5,282,473 | A * | 2/1994 | Braig ..................... | A61B 5/083 250/343 |
| 6,791,088 | B1 * | 9/2004 | Williams, II ......... | G01M 3/047 250/343 |
| 2003/0205673 | A1 * | 11/2003 | Williams ................. | G01J 3/12 250/343 |
| 2005/0268690 | A1 * | 12/2005 | Weckstrom ........ | G01N 21/3504 73/23.2 |
| 2008/0204757 | A1 * | 8/2008 | Manning ................... | G01J 3/02 356/451 |
| 2010/0133435 | A1 * | 6/2010 | Maillart ............. | G01N 21/3504 250/338.5 |
| 2010/0219960 | A1 * | 9/2010 | Moe .................... | G01N 33/0032 340/632 |
| 2010/0258728 | A1 * | 10/2010 | Wong ................. | G01N 21/3504 250/339.13 |
| 2015/0028209 | A1 * | 1/2015 | Harju .................... | G01M 3/222 250/338.5 |

FOREIGN PATENT DOCUMENTS

EP    0733341    * 9/1996

* cited by examiner

*Primary Examiner* — Yara B Green
(74) *Attorney, Agent, or Firm* — J. Douglas Wells

(57) ABSTRACT

A handheld-sized, single-hand-holdable, single-hand-operable battery-powered gas leak detector that draws in a sample of ambient air for detecting the presence of a gas by sensing changes in infrared (IR) energy between an IR emitter and an IR sensor when the gas is in the space between the IR emitter and the IR sensor. An algorithm is used that triggers detection of a gas when the change in IR energy between the IR emitter and the IR sensor is more rapid than the thermal drift of the IR sensor, and the detector design allows for IR energy within a wide range of approximately 0.4 micrometers to approximately 20 micrometers to pass into the air being sampled.

20 Claims, 6 Drawing Sheets

LEAK DETECTOR

CROSS-REFERENCE TO RELATED APPLICATIONS

None.

BACKGROUND OF THE INVENTION

The technical field of invention relates to a leak detecting device for detecting presence of a gas. More particularly, the present invention pertains to a hand-held, single-hand-sized leak detecting device for general hazardous gas detection or air-borne sampling and detecting the presence of a specific gas.

Several different designs of leak detectors have been disclosed in various publications. The different designs are directed to provide potential solutions to particular problems. For example, US patent application publication no. US 2015/0028209 by Harju et al. ("Harju"), published Jan. 29, 2015, with assignee identified as Fieldpiece Instruments, Inc., discloses a refrigerant gas leak detector that incorporates a two-part unit—a first (handle) portion consisting of a gas sampling chamber and an infrared (IR) optical detector specific to detecting bandpass filtered IR energy within the range of 7 to 14 microns, and a second portion (presumably managed with the user's second hand, with the user's first hand holding the first/handle portion) connected to the first portion by a flexible tube, the second portion consisting of a suction pump, signal processing, and battery power components. The two-part design in Harju is disclosed as a solution to the problem of false triggering due IR emitter sensitivity to the vibration of the pump motor and to IR emitter sensitivity to pressure fluctuation from the pump. The two-part design places the IR emitter in the handle portion and the pump motor in the second portion, connected by three feet of flexible hosing, thereby dampening pump vibration and pressure fluctuation.

Harju also discloses an embodiment of an IR leak detector that utilizes a single housing for all the leak detector components—including the gas sampling chamber, the optical detector with bandpass filter for allowing IR energy within the range of 7 to 14 microns to pass (and attenuating energy outside of that range) between the IR emitter and IR sensor, the signal processing components, and (presumably, but not shown in figures or clearly described) the suction pump, and associated battery power. Harju discusses detection of refrigerants that absorb wavelengths of IR light primarily in the 8-10 micron range, and preferred detector designs having a 7 to 14 micron bandpass IR filter formed integrally with the IR sensor, which Harju discloses as being directed to the detection of refrigerants such as hydrofluorocarbons (HFCs), hydrochlorofluorocarbons (FCFCs), and chlorofluorocarbons (CFCs).

Harju further discusses disclosures in Williams, I I et al. U.S. Pat. No. 7,022,993 and Williams, I I et al. U.S. Pat. No. 6,791,088 (collectively, "Williams"), both reexamined (with all claims in the '088 patent cancelled and claims 2-3, 6-7, and 9 determined patentable in the '993 patent) and having the assignee identified as Twin Rivers Engineering, Inc., that describe gas leak detector designs incorporating optical filtering to block IR energy that is absorbed by water vapor and other gases at wavelengths that are 6 microns and below, to reduce false triggering. The Williams gas leak detector designs include a (first) filter next to the IR emitter for blocking IR energy from approximately 6 microns down through the sampling chamber, and another (second) filter in front of the IR sensor for allowing a selected IR energy range of approximately 8 to approximately 10 microns to pass through the sampling chamber, with the IR sensor arranged for detecting resultant IR energy from the first filter and the second filter. Like Harju, Williams discloses designs directed to gas leak detection of HFCs, HCFCs, and CFCs. In addition, Williams lists numerous other compounds that can be detected, although Williams does not disclose the specific design changes needed for detection of such additional compounds. The additional compounds listed in Williams include: refrigerant blends, propane, methane, gasoline, ammonia, acetone, benzene, bromine, carbon dioxide, carbon monoxide, chlorine, fluorine, hydrogen sulfide, isobutyl alcohol, isopropyl ether, pentane, sulfur dioxide, sulfur hexafluoride, trichloroethane, vinyl acetate, vinyl bromide, and xylenes.

Both the Harju and Williams designs provide audible indication for gas leak detection. Harju includes a beeper that provides an audible signal when a leak is detected. The Williams design includes an audio output to the detector for emitting an audio signal from a detected leak, the audio output having a 1 Hz chirp rate that digitally shifts to a 2 Hz chirp rate upon detection of the gas leak. The chirp rate increases above the 2 Hz rate in proportion to the size of the gas leak being detected.

Both the Harju and Williams designs include gas leak detection by way of sensing a gas within a chamber between an IR emitter and an IR sensor/detector, with signals from the IR sensor/detector used to determine presence of a target gas to be detected. Harju discloses signal processing circuitry in very general terms that include circuitry for receiving and amplifying IR sensor output signals that are then input to a central processing unit (CPU). The CPU receives control signals from an external controls device and provides output signals to a display, status indicator lights, and to a beeper for an audible signal when a gas leak is detected. The Williams gas leak detector includes a signal detection accumulator in the detector with a forward biased detector circuit, and a zero circuit in the detector referenced to approximately a circuit ground instead of referenced between supply rails. Signals from the detection accumulator are directed to LED drivers for LED display and to a tone chirp rate generator for driving a piezo speaker.

Another IR instrument designed for the detection of contaminants in ambient air is the INFRARAN (trademark) specific vapor analyzer by Wilks Enterprise, Inc. ("Wilks"). The Wilks analyzer is a portable device and is larger (at 15"×7.3"×7.5") and heavier (at 18 pounds) than either of the much smaller hand-held designs disclosed in Williams and Harju. Operation is two-handed, with one hand for carrying the 18 pound main body, and the other hand positioning an air sampling wand connected to a flexible tube leading back to the main body. The Wilks design provides an analyzer that can be purchased to measure a compound that has an absorption band in the IR range from 2.5 to 14.5 microns. The design uses fixed bandpass filters in the IR optics. An integral air pump draws the sample gas into a cell (chamber) having two mirrors, one on each of two opposite sides of the cell. An IR emitter and an IR detector are positioned aft of one of the mirrors on one side of the cell, with supporting amplifier and signal processing circuitry for receiving output from the IR detector, and a CPU, control inputs, display outputs, and (battery or AC) power management circuitry. The air pump draws the sample into the cell, and the sample absorbs the IR energy from the IR beam (that is bounced back and forth within the cell between the two mirrors). The IR detector measures the amount of energy absorbed at the selected wavelength, and the microprocessor converts it into a concentration (ppm or percent) for display. The Wilks product brochure lists the following as gases that can be detected and measured: acetone, carbon dioxide (absolute), carbon monoxide, carbon tetrachloride, desflurane, general hydrocarbons (hexane), isoflurane, isopropyl alcohol, methylene chloride, nitrous oxide, perchloroetylene, R 114, R 12, R 134A, R 236 fa, sevoflurane, sulfur hexafluoride, and toluene.

Each of the existing IR gas detector designs has disadvantages in terms of cost, complexity of design, ease of use, range of IR energy detected, method of audible alarm, form factor and ergonomics of the device, design aesthetics, and/or other factors. What is needed are designs for a hand-held, single-hand-sized leak detecting device for general hazardous gas detection or air-borne sampling and detecting the presence of a specific gas that address one or more disadvantage of existing designs.

The foregoing and other objectives, features, and advantages of the invention will be more readily understood upon consideration of the following detailed description of the invention taken in conjunction with the accompanying drawings.

BRIEF DESCRIPTION OF THE SEVERAL DRAWINGS

For a more complete understanding of the present invention, the drawings herein illustrate examples of the invention. The drawings, however, do not limit the scope of the invention. Similar references in the drawings indicate similar elements.

DETAILED DESCRIPTION OF PREFERRED EMBODIMENTS

In the following detailed description, numerous specific details are set forth in order to provide a thorough understanding of the preferred embodiments. However, those skilled in the art will understand that the present invention may be practiced without these specific details, that the present invention is not limited to the depicted embodiments, and that the present invention may be practiced in a variety of alternate embodiments. In other instances, well known methods, procedures, components, and systems have not been described in detail.

Figure 3:
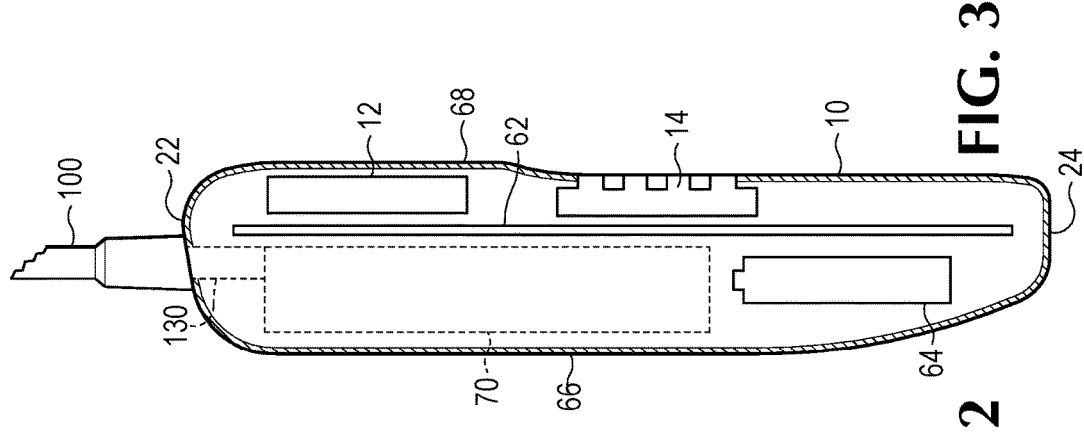
FIG. 3 illustrates a cutaway side view of the gas leak detector in FIG. 1, according to various preferred embodiments.
Figure 2:
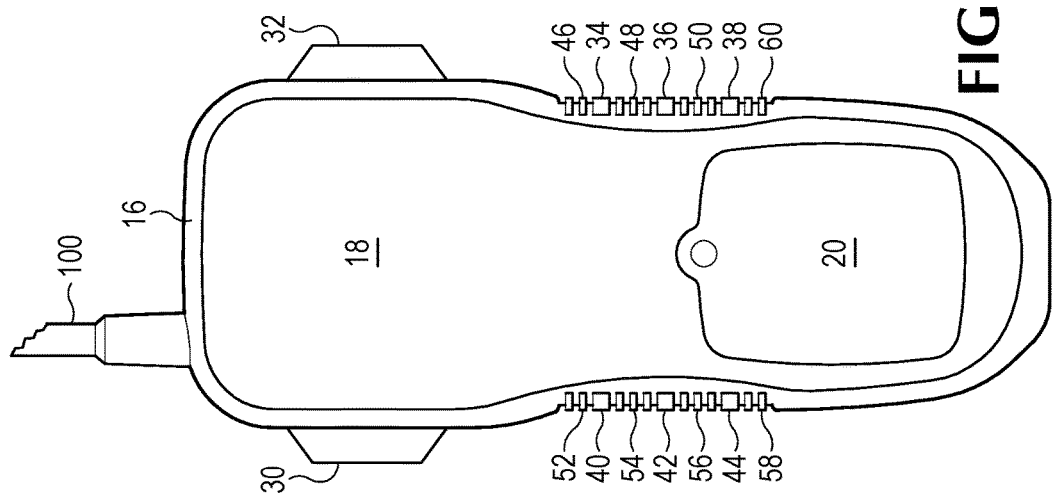
FIG. 2 illustrates a back view of the gas leak detector in FIG. 1, according to various preferred embodiments.
Figure 1:
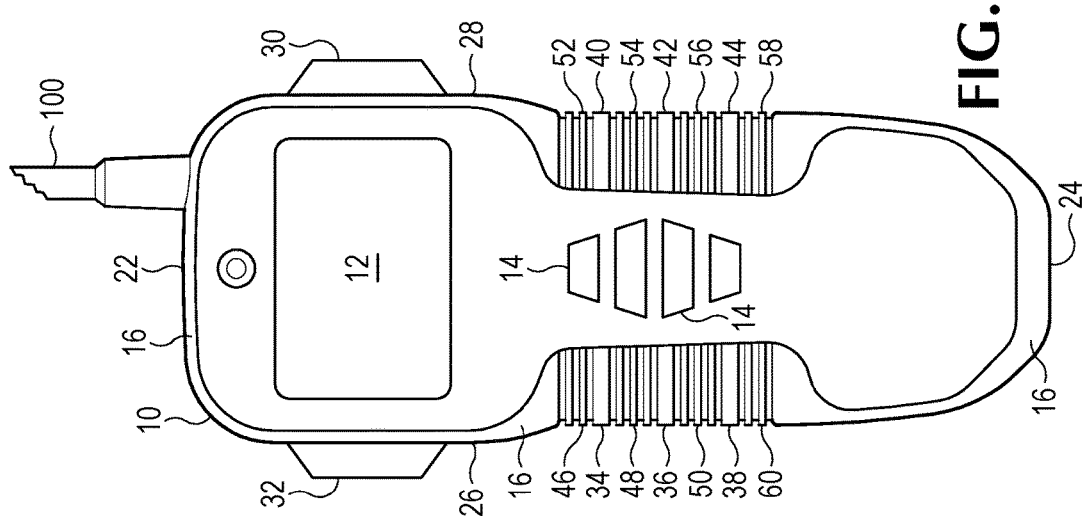
FIG. 1 illustrates a front view of a hand-held, single-hand-sized infrared (IR) gas leak detector, according to various preferred embodiments.

Preferred embodiments comprise a handheld-sized, single-hand-holdable, single-hand-operable battery-powered gas leak detector that draws in a sample of ambient air for detecting the presence of a gas by sensing changes in infrared (IR) energy between an IR emitter and an IR sensor when the gas is in the space between the IR emitter and the IR sensor. A preferred ergonomic form-factor for such a gas leak detector is illustrated in FIGS. 1, 2, and 3, with FIG. 1 showing a front side of such device 10, FIG. 2 showing a back side, and FIG. 3 depicting a side cutaway view revealing various internal components of such device 10.

In one embodiment, the IR gas detector 10 comprises an optical device referred to as the "bench," housed within the space 70 and supported by an electronic circuit board 62 that is capable of discriminating changes in the thermal sensor section of the bench. The bench preferably comprises a hollow sample tube 140 as diagrammed in FIG. 4, that is capped and sealed at each end by a housing that mounts an infrared radiation source (IR emitter 150) and an IR optical filter 190 at one end and a thermal sensor 160 with two IR optical filters 170, 180 at the other end. The bench air path is preferably sealed from the emitter and sensor by the IR filters which slows undesirable heat transfer by convection from the sample air stream. Because the emitter 150 may reach temperatures that could ignite many gasses, a sealed IR filter/emitter combination also provides isolation from combustible gasses as they pass through the bench.

From the sample tube 140 there are preferably two small tubes, one connecting to the detector air sample inlet and the other to a small air pump 120. The pump provides suction (for example, at a flow rate of 100 cc/min.) for the air sample that passes through the bench. The inventor discovered it is possible to deplete the gas from a very small leak if too much air is taken in, and the inventor determined an intake flow rate of 100 cc/minute is preferred. The gas sampling inlet 100 is preferably a flex tube for positioning its tip into hard to reach places. The inventor determined the inside diameter of the inlet tube 100 is preferably small so as to accelerate/speed the passage of the sample air or air and gas mix. In addition to a small inside diameter of intake tube 100, there is preferably a moisture blocking filter within the inlet tube 100 that prevents contamination from reaching the IR optics within the bench. In one embodiment, a visible filter media is used in the intake tube 100 that turns blue when it becomes wet, letting the user know of the contaminants in the sample air.

The detection process preferably comprises focusing the IR emitter 150 beam on the IR detector 160, whereupon the sensor 160 reacts to heat generated by the IR beam. In operation, and in accordance with preferred embodiments, with a sample nozzle 100 intaking "clean air", the thermal sensor stabilizes and the gas detector 10 generates a "normal" audio signal every two seconds to indicate that the gas detector 10 has warmed up and is not sensing a change in the air passing through the bench. Preferably the sensor output signal only responds to a change in temperature at the sensor element. In practice, as discovered by the inventor, there are two primary causes of a change in temperature at the sensor. First is the amount of IR radiation that is shining on the sensor element. The second primary cause is undesirable and is a result of the environment, including the temperature of the sample air stream and housing, and causes the thermal sensor to drift.

When air passing through the bench contains a detectable gas, the gas molecules absorb some of the IR radiation and convert the absorbed IR energy to kinetic energy. The result is a cooling of the IR sensor as less IR energy strikes the sensor. The amount of absorption is a function of the gas type and the concentration of the gas, and the absorption increases as the natural log of the concentration. When the reduction of heat reaches the sensor 160, the device 10 preferably generates a signal proportional to the cooling, and the device 10 preferably stops the "normal" tone and generates a high pitched audio tone to indicate detection of gas. Non-symmetrical gas molecules will absorb IR energy at various wavelengths relative to their chemistry and density. Different gasses absorb IR energy at different IR wavelengths, and the amount of absorption is different for different gasses.

In various embodiments, different IR filters may be used to tune the gas detector 10 for various gas compounds. Preferably, the IR optical filters in the device 10 limit the wavelength of IR energy that passes through the bench to approximately 1-20 micrometers. Additionally, the IR filters (along with the air space between the filters and the emitter or sensor) provide significant thermal isolation for the IR emitter 150 and the thermal sensor 160 from the stream of air passing through the bench sample tube 140. The cooling of the thermal sensor 160 when a gas enters the bench, the inventor determined, is a small fraction of a degree. The "thermal sensor can," the inventor discovered, is as sensitive to thermal changes as the sensor element. Therefore, the inventor determined, the housing preferably needs to maintain a stable temperature. And the inventor further discovered that the particular temperature of the housing does not matter as long as the temperature of the housing is maintained as stable as possible. In practice, as the inventor discovered, there is always some thermal drift.

The inventor determined that it is practically impossible, or at least unnecessary, to control the thermal drift of the environment that the gas detector 10 is exposed to, and the thermal drift of the sensor housing is preferably slow compared to the reaction inside the bench to gas entering the sample tube 140. In one embodiment, double IR optical filters 170, 180 provide the additional function of reducing thermal drift of the sensor housing. The inventor determined adequate insulation provided by the plastic housing of the gas detector 10 is preferred, to further reduce thermal drift of the sensor housing.

Additionally, the inventor discovered simple bending of the bench slightly will cause signal changes that could be interpreted as a gas detection signal, so mounting the bench so as to minimize distortion of the bench when normally handled, is preferred. In one embodiment, a floating mounting of the bench is used. For example, the space 70 within which the bench is preferably disposed within the plastic housing as shown in FIG. 3 having back and front sides 66, 62 and bottom and top ends 24, 22 in a way that maintains the rigidity of space 70, with space 70 floatably secured within the plastic housing so that distortions of the plastic (outer) housing do not transfer to distortions of the space 70 comprising components of the bench. In another embodiment, the inventor determined one way to obtain sufficient stability of the bench structure is to cast the bench into the molded housing of the gas detector 10. For example, the space 70 and components comprising the bench may be integrally molded into the rigid plastic housing of the gas detector 10 shown in FIG. 3.

The power for the IR gas leak detector 10 preferably comprises batteries 64, such as four (4) AA alkaline batteries accessible via a battery cover 20 on the back side 18 of the device. The inventor determined the main power draw of the leak detector 10 is the IR emitter 150, followed by the air pump 120. Battery voltage is preferably regulated by both linear and switching regulators.

Figure 5:
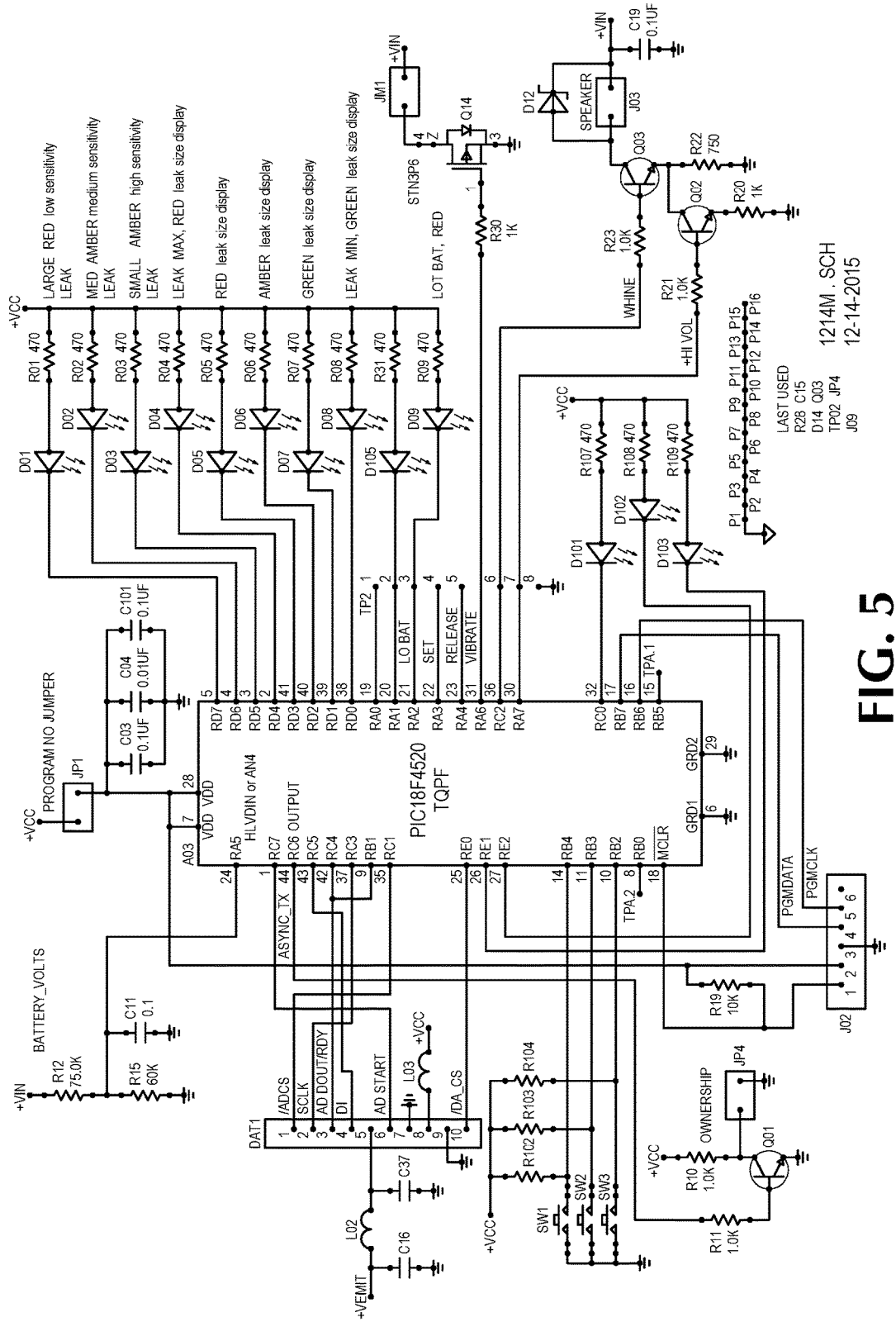
FIG. 5 is a schematic of circuitry comprising the microcontroller section of the main circuit board for the gas leak detector of FIG. 1, according to preferred embodiments.
Figure 6:
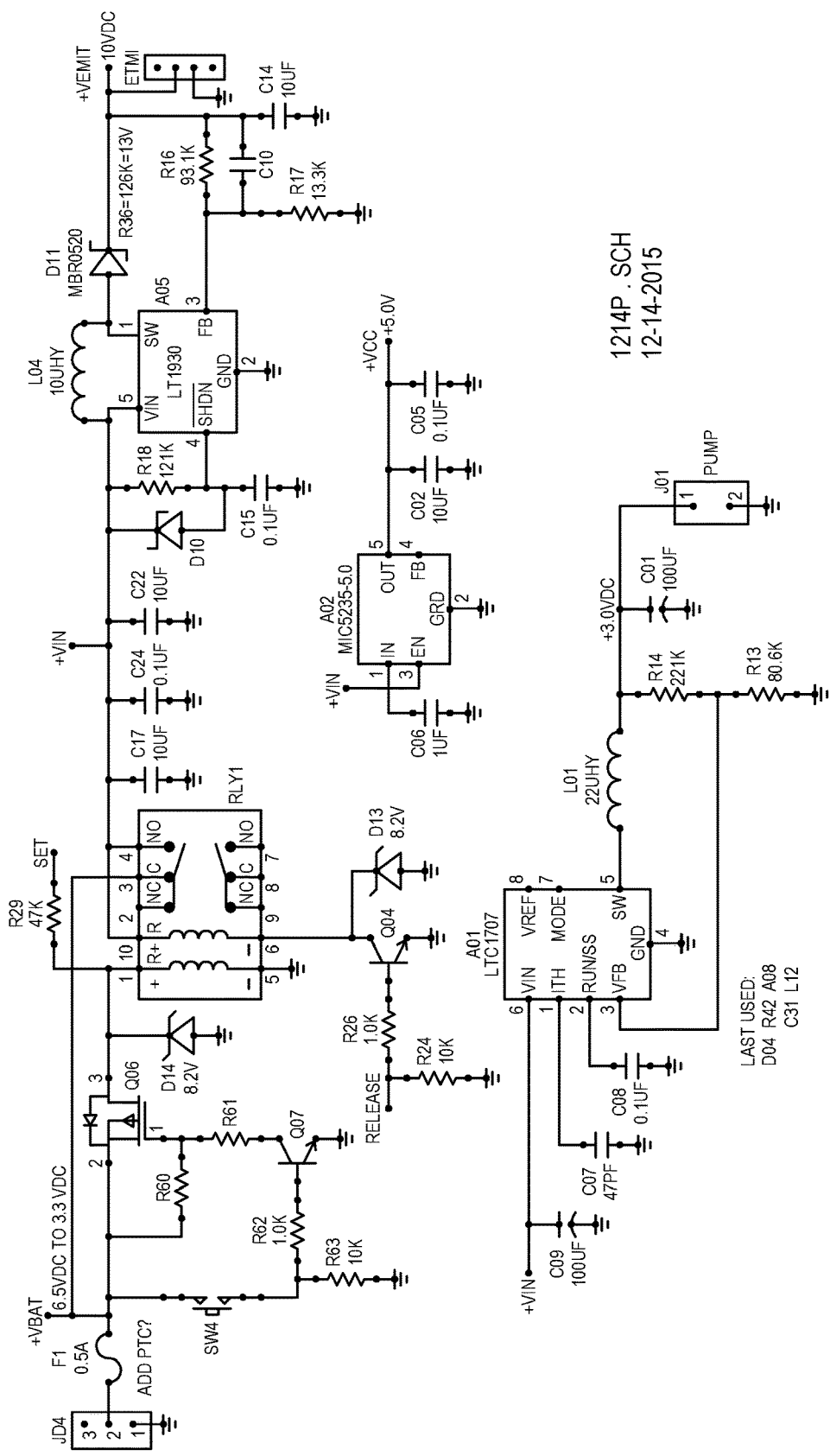
FIG. 6 is a schematic of circuitry comprising the power section of the main circuit board for the gas leak detector of FIG. 1, according to preferred embodiments.
Figure 7:
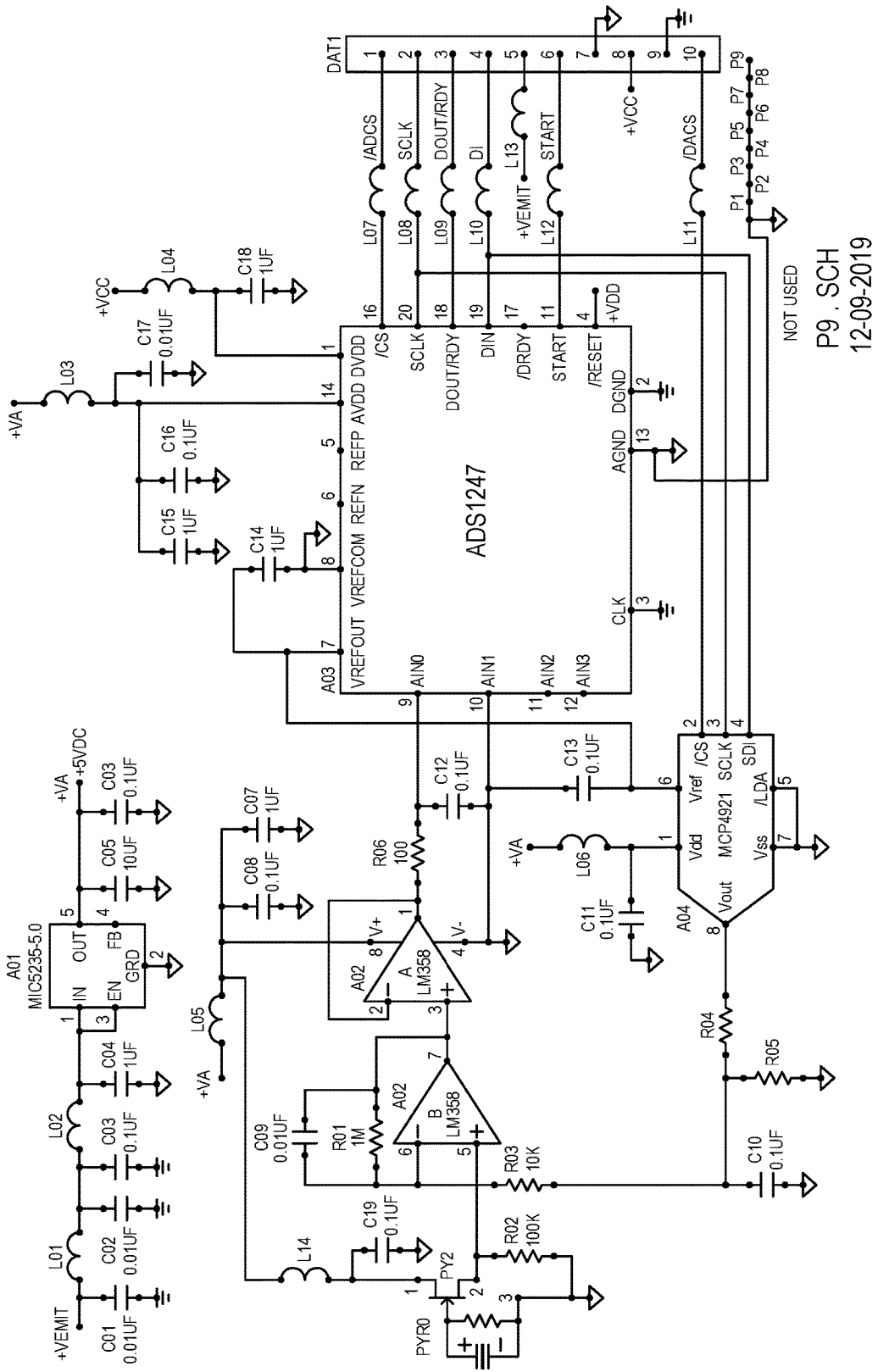
FIG. 7 is a schematic of circuitry comprising the sensor section of the separate, sensor-end-of-the-bench circuit board for the gas leak detector of FIG. 1, utilizing a pyro-electric type detector, according to preferred embodiments.
Figure 8:
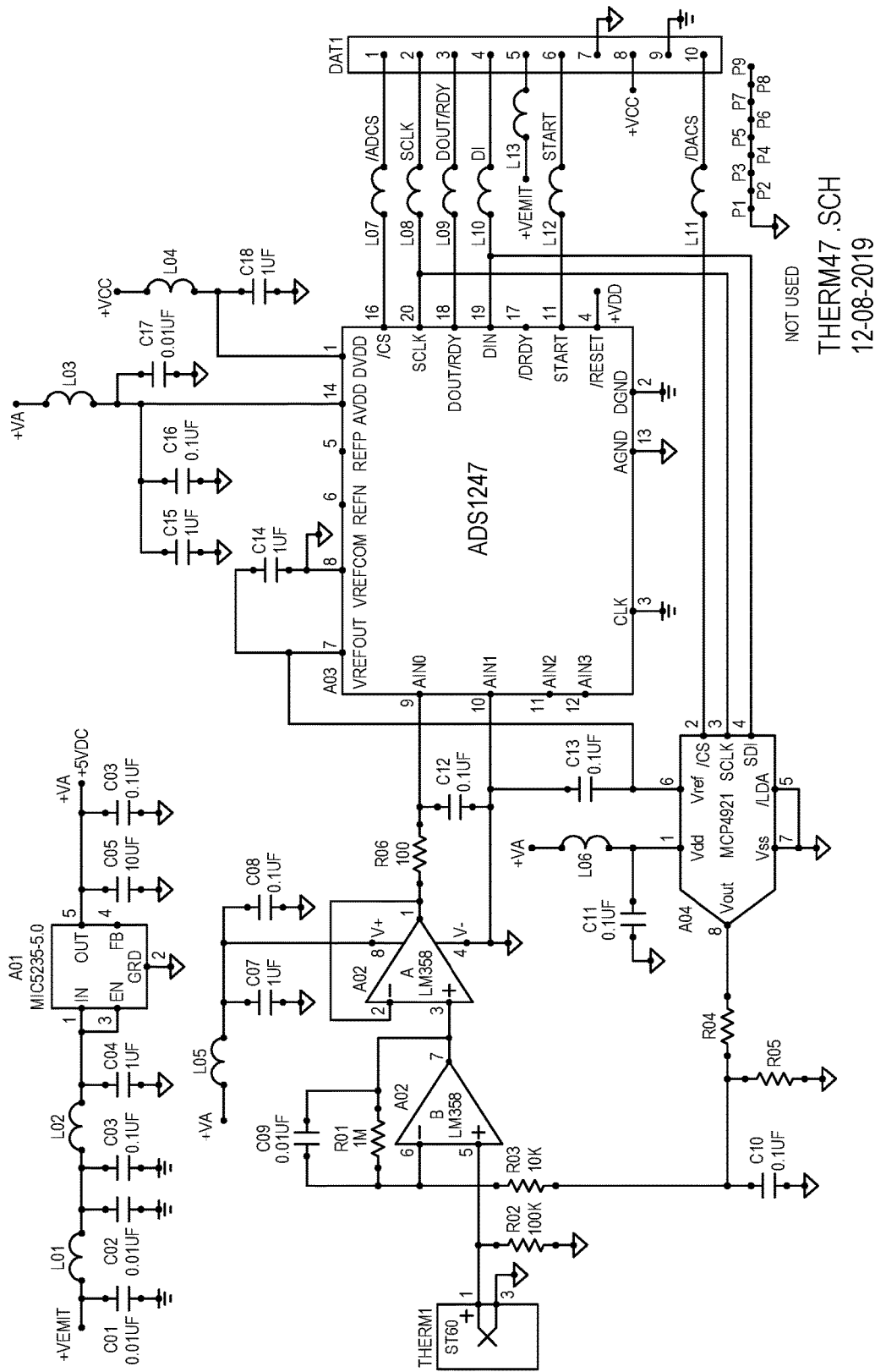
FIG. 8 is a schematic of circuitry comprising the sensor section of the separate, sensor-end-of-the-bench circuit board for the gas leak detector of FIG. 1, utilizing a thermopile type detector, according to preferred embodiments.

FIGS. 5, 6, 7, and 8 are exemplary schematics for circuitry comprising a gas leak detector such as device 10, according to various embodiments. FIG. 5 shows a circuitry labeled "X214M" comprising the microcontroller section of the main circuit board 62 for device 10, and FIG. 6 shows circuitry labeled "X214P" comprising the power section of the main circuit board 62 for device 10. Both the microcontroller section and power section circuitry are preferably located on the main circuit board 62, and circuitry comprising the sensor section is preferably on a separate circuit board located at the sensor end of the bench. FIG. 7 shows circuitry comprising the sensor section of the separate, sensor-end-of-the-bench circuit board for the gas leak detector 10, utilizing a pyro-electric type detector. And FIG. 8 shows circuitry comprising the sensor section of the separate, sensor-end-of-the-bench circuit board for the leak detector 10, utilizing a thermopile type detector (instead of the pyro-electric type detector).

Additional circuitry (not completely shown in the schematics shown in FIGS. 5-8) is preferably included to provide a tactile feedback (i.e. vibration) for the user, to indicate a gas detection event. Preferably, the level of vibration output increases as the gas concentration detected increases. The larger the gas leak, the more/stronger vibration of the device 10 output to the user.

The sensor section circuitry preferably includes a 24 bit analog to digital converter that samples the (pyro-electric or thermopile type) thermal sensor signal. The can that mounts the pyro-electric sensor, for example, is preferably sealed with an integral IR optical filter window. Different IR filters may be used to tune the detector for various gas compounds. The sensor housing preferably also mounts a second filter with an insulating washer between them, providing the spacing to ensure an insulating air gap between the sensor can and the second filter. The inventor discovered that the washer minimizes the heat transfer from the second filter to the sensor can, thereby further improving sensor performance. The inventor determined that successful gas detection is improved when the thermal drift of the sensor is slow as compared to the IR absorption caused by the gas concentration. The inventor discovered that this allows the gas detection algorithm to ignore the slow drift that is normal for the sensor and to detect the rapid decrease in IR heating of the sensor element caused by a gas entering the bench.

Turning back to FIGS. 1-3, several innovative features of a single-hand sized gas detector 10 are illustrated. As shown, the detector 10 preferably comprises a main body or plastic housing having a longitudinal length from a bottom or rear most surface 24 to a top or forward most surface 22, and having a transverse width from a left surface 26 to a right surface 28. In one embodiment, the longitudinal length 22-24 is approximately 171.5 mm, and the width left to right 26-28 is approximately 69.8 mm. Extending forward from the main body is the intake tube or intake probe 100 (shown partially). Extending outward from each side near the forward portion of the device 10 where an output display 12 is positioned, are, as shown, right and left extensions, 30 and 32, respectively, configured and sized for holding the device 10 in various device holding accessories (not shown). On the front center portion of the device 10 are positioned one or more (preferably four) navigation buttons 14 for use in operating the leak detector/device 10. In some embodiments, the navigation buttons 14 are usable in connection with output presented by the display 12 to access and select from menu options.

To aid in handling the device 10 and for improved and unique aesthetics of the device 10, a rubber or similarly grip improving material 16 is preferably formed around the sides and top and bottom surfaces, as shown. In one embodiment, the grip material 16 covers the sides, top, and bottom, and leaves the front and rear (back side 18) portions of the main body uncovered. In preferred embodiments, the grip material 16 areas and the uncovered main body portions are of contrasting colors. For example, the grip material 16 may be black or dark grey, and the uncovered main body portions may be a contrasted color such as yellow, or orange, or another contrasted color.

Also included for improved handling and to aid with using the device 10 with a single hand, are side grip ridges 46, 48, 50, 60, 52, 54, 56, and 58. The side grip ridges preferably comprise matching pairs of right and left ridges, for example ridges 52 and 46, 54 and 48, 56 and 50, and 58 and 60. The side grip ridges also provide a unique and iconic pattern that may provide a source identifying (or trademark) function for the device. For example, the pattern—two ridges 46, a larger section 34, three ridges 48, a large section 36, three ridges 50, a large section 38, and finally two ridges 60—a "2-3-3-2" ridge/surface grip pattern—is used on several devices manufactured and distributed by Universal Enterprises, Inc. The 2-3-3-2 pattern is preferably repeated on both left and right sides. As shown, the 2-3-3-2 ridge/surface grip pattern comprises a left side pattern—two ridges 46, a larger section 34, three ridges 48, a large section 36, three ridges 50, a large section 38, and finally two ridges 60—and a corresponding and matching right side pattern—two ridges 52, a larger section 40, three ridges 54, a large section 42, three ridges 56, a large section 44, and finally two ridges 58.

The cutaway side view of the gas leak detector 10 in FIG. 3 depicts the device 10 having a longitudinal length from a bottom surface 24 to a top surface 22, and a thickness from a front surface 68 to a back surface 66. In preferred embodiments, a flexible tube 130 provides an air passage from the intake probe 100 to the bench and pump components within the space 70, the space 70 preferably positioned just aft of the intake probe 100 toward the back side of the main body. The bench and pump space 70 preferably has approximate dimensions 2.25"×3.625"×0.75". Preferably below the bench and pump space 70 is a space for the batteries 64, and the main circuit board 62 is positioned in front of the bench and pump space 70 and batteries 64. The main circuit board 62, in one embodiment, is approximately 2.25"×6.25". Preferably in front of the main circuit board 62 opposite the bench and pump space 70 is a display or LED inset 12, and in front of the main circuit board 62 opposite the bench and pump space 70 and positioned in the central portion of the front side of the device 10, are the navigation buttons 14.

Turning back to FIG. 4, the detailed components and operation of the gas detector 10 may be different in various embodiments. The following provide additional details for the components diagrammed in FIG. 4, according to various embodiments.

The intake probe 100 may be flexible or rigid, and is for drawing in the air being tested. The intake probe 100 preferably extends outward from the top surface 22 of the main body of the leak detector 10. Preferably a filter protects the optics within the bench from liquids and dust. The inventor discovered the IR detector works best when the tip of the intake probe 100 is used in a sweeping motion to test an area for a gas leak, the tip passing from clear air to contaminated air.

The air pump 120, in preferred embodiments, is used to draw air in through the intake probe 100, through a flexible hose 130, and through the sample tube 140. Suction provided by the air pump 120 draws in an air sample from an area suspected of leaking gas, at a rate that, as the inventor discovered, maximizes the response of the IR sensor 160 to the step change in incident IR radiation that occurs when the sample air is contaminated by a hazardous gas.

Preferably, a flexible hose 130 connects the intake probe 100 with the optical bench. As shown, a flexible hose 130 connects the intake probe 100 to an inlet of the sample tube 140 near the IR emitter 150, and another flexible hose 130 connects the pump 120 to an outlet of the sample tube 140 near the IR sensor 160.

The sample tube 140 is preferably a small diameter tube that contains the IR energy and allows the IR energy to interact with the air sample. The inventor discovered, contrary to some teachings, a highly polished finish inside the sample tube 140 is not required due to the short path length within the sample tube 140. The sample tube 140 is preferably configured with an inlet located at the IR emitter 150 end of the sample tube 140, and an outlet located at the IR detector 160 end of the sample tube 140.

The IR emitter module 150 preferably comprises a resistive IR generator coupled through a wide band IR filter 190 to one end of the sample tube 140. The IR emitter 150 is preferably highly insulated and allows the maximum IR energy to interact with the air sample. The IR emitter 150 is preferably thermally isolated from the gas stream convection via the single wide band filter 190. In preferred embodiments, the IR emitter 150 comprises a resistor that is heated to generate infrared (IR) emissions in the 0.4 to 20 um wavelength range, and the voltage that drives the IR emitter 150 is regulated, unlike teachings in other patent disclosures. Additionally, the IR emitter 150 may have an integral thermistor for feedback to the regulator, to allow for consistent heating regardless of the ambient temperature.

The IR detector/sensor module 160 preferably comprises a highly sensitive commercially available IR sensor such as a thermopile or a pyro-electric detector, and is positioned at the opposite end of the sample tube 140, opposite from the IR emitter 150. The IR detector/sensor module 160 is preferably highly insulated from ambient air and the air sample. The IR sensor is preferably thermally isolated from the gas stream convection via two IR filters 170, 180. The output of the IR sensor 160, the inventor discovered, will drift due to heat transfer from the air flow in the sample tube. This drift, the inventor determined, may be reduced by careful insulation of the optical bench and is thereafter of no consequence and may be ignored. The IR sensor 160 responds to a change in the receive amount of IR radiation and produces a proportional output signal.

DC coupled buffer electronics are preferably included (co-located with the IR sensor 160) to reduce the output impedance of the IR sensor 160 (to provide a low impedance drive to the analog to digital converter 200), and the analog to digital converter 200 may also be co-located with the IR sensor 160.

An optional version of the IR sensor module 160 incorporates either dual or quad IR sensors in one package, with each independent sensor/detector having a unique IR filter 170.

Figure 4:
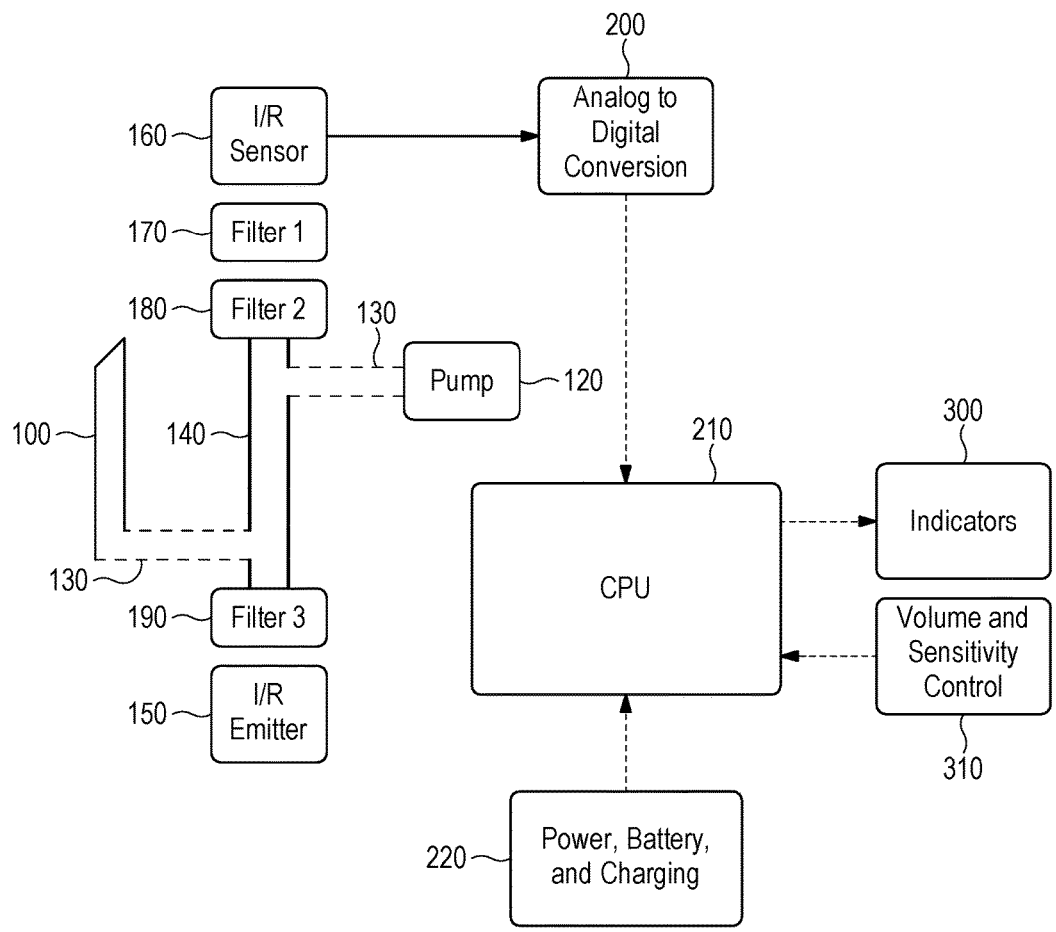
FIG. 4 is a functional block diagram of an infrared (IR) based gas detector, according to various embodiments.

The filter 170 shown as "Filter 1" in FIG. 4 is preferably physically insulated from both "Filter 2" 180 and the IR detector 160 to minimize heat transfer from the air sample, and may be a wide band 0.4 to 20 micrometer wavelength filter for general hazardous gas detection, or optimized to detect a specific gas. In preferred embodiments, the IR filter 170 is integral with the IR sensor 160 package (or multiple unique IR filters are integral with the IR sensor package if dual or quad sensors are used).

The filter 170 may be a wide band or a narrow band filter depending upon the application. Other IR gas leak detector related patent disclosures specifically exclude the band of IR wavelengths between 0.4 and 6 um (microns or micrometers), which means those leak detector designs, the inventor determined, cannot detect methane, carbon monoxide (CO), and carbon dioxide (CO2). Preferably the gas leak detector 10 comprises a wide band hazardous gas detector and is capable of detecting many gases.

Alternately, if CO2 or CO is the desired gas, or both gases, the filter 170 passes wavelengths in the range 4-5 um. If a methane detector is desired, the filter centers on approximately 3.3 um.

The filter 180 shown as "Filter 2" is preferably physically insulated from "Filter 1" 170 to minimize heat transfer from the air sample, and may be a wide band 0.4 to 20 micrometer wavelength filter for general hazardous gas detection or optimized to detect a specific desired gas. Filter 180 preferably precedes the IR sensor 160 and may be either a wide band or narrow band filter depending upon the application.

The filter 190 shown as "Filter 3" is preferably a wide band passing 0.4 to 20 micrometer wavelength filter, and positioned to insulate the IR emitter 150 from the air sample. The wide band filter 190, the inventor discovered, provides temperature insensitivity.

In one embodiment, only one filter, Filter 1 170, is used, and the other two filters (Filter 2 180 and Filter 3 190) are not included in the leak detector 10; and the filter 170 comprises an IR band pass filter that allows passage of IR wavelengths within the range of approximately 0.4 um to approximately 20 um. The inventor determined this embodiment (having only one IR band pass filter 170) to be a lower cost version and most suitable for detection of inert gases such as CO2.

In a second embodiment, only two filters, Filter 1 170 and Filter 3 190, are used, and the other filter shown in FIG. 4 (Filter 2 180) is not included in the leak detector 10. The inventor determined this embodiment (having two band pass filters 170, 190 with one in front of the IR emitter 150 and the other in front of the IR sensor 160, and each filter allowing passage of IR energy within the range of 0.4 um to 20 um) to be effective for hazardous leak detection.

In a third embodiment, all three of the filters shown in FIG. 4, Filter 1 170, Filter 2 180, and Filter 3 190, are used as previously described; and in this embodiment, Filter 3 190 may be selected with a narrower band to detect a specific gas or gases.

The analog to digital conversion 200 preferably comprises a high resolution analog to digital converter (ADC) that is DC coupled to the IR sensor 160 output, and in preferred embodiments it is not necessary to zero, accumulate, or hold the signal. Preferably, the leak detector 10 circuitry does not "accumulate" the signal, instead utilizing an analog to digital converter to provide continuous real-time sampling of the signal from the IR sensor 160 so that the device 10 does not have or require any analog accumulation or forward biased detector circuit. Moreover, a zero circuit is not necessary or included. A digital to analog converter is used to softly keep the signal in the linear detecting range of the ADC; detection occurs when the digital value of the signal makes a more rapid change than the normal thermal drift of the IR sensor 160, caused by the change in concentration of a detectable gas. Conversion of IR energy to kinetic energy by the gas compounds that are drawn through the sample tube 140 and the subsequent reduction in IR energy, is detected by the IR sensor 160 and converted to a digital value by the high resolution ADC 200.

The CPU or microcontroller or microprocessor 210 is preferably configured to discriminate the digitized signal received from the ADC 200. The digital signal from the ADC 200 is preferably evaluated by the microprocessor 210, and the processor 210 reacts to the signals based on a discrimination algorithm. Preferably, the normal slower drift of the IR sensor 160 is ignored and a rapid reduction of the IR at the sensor 160, due to gas absorbing the IR energy in the sample air, is designated as a valid gas detection. Preferably software determines the size of the gas leak detected and in the case of multiple detectors, what band the detected gas resides in. An example is a hazardous gas detector that detects methane, carbon dioxide, carbon monoxide, and one of several refrigerants.

The power, battery, and charging 220 preferably includes various voltage regulators to provide power to the gas leak detector 10. The microprocessor 210 preferably monitors the battery charge condition.

The indicators 300 preferably comprise LED or LDC display indicators of the condition and operating state of the leak detector 10, an indication of the magnitude of the signal, indicators to indicate if the detector is in the measure of locate mode, as well as a low battery indication. The indicators 300 preferably comprise a speaker to provide a three tone idle signal every two seconds when the unit is not detecting a hazardous gas. When a gas is detected, the indicator changes to a high pitch squeal, with the frequency increasing with increased gas concentration detection. A non-detection operation is preferably indicated by a three tone "doo-dee-doo" every two seconds. This indicates the device 10 is warming up and operating. The three tone indication preferably changes to a high pitched squeal of 2000 Hz and up upon detection of a detectable gas, the audible signal comprising a tone and not a chirp. The indicators 300 preferably further comprise a vibrator for a tactile indication of a sensing event, with the intensity increasing relative to the concentration of the gas. The tactile indication is useful when the indicators cannot be seen or heard.

The volume and sensitivity control 310 preferably comprises volume control via short activations of the on/off button. Preferably the on/off function is by way of holding the button for three seconds. In some embodiments, there are two sensitivity adjustment controls. One button causes the detector PG2 to step through predetermined detection windows. The other sensitivity control places the hazardous gas detector 10 in the "Locate" mode and significantly increases the sensitivity so that the unit 10 can "sniff" for low concentrations of gas. Preferably an indicator lights to indicate the mode of operation. In preferred embodiments, four buttons control the device 10—power on/off, sensitivity control, mute on/off, and peak hold.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A single-hand operable, single-hand sized, handheld portable gas leak detector comprising:
   (a) a single-hand sized housing enclosure having an interior volume and having a length, a width, and a thickness, the length extending longitudinally from a bottom surface to a top surface, the width extending from a left side surface to a right side surface, and the thickness extending from a back side surface to a front side surface;
   (b) an intake probe tube extending away from the interior of the housing enclosure;
   (c) an optical bench disposed within said housing enclosure that includes an air sample tube having an infrared (IR) emitter module at one end of the air sample tube and an IR sensor module at the opposite end of the air sample tube, an inlet near said IR emitter module fluidly connected with said intake probe tube, and an outlet near said IR sensor module fluidly connected with an air pump within said housing enclosure via a flexible tube, said optical bench being insulated from bending within said housing enclosure;
   (d) said IR sensor module having a wide band optical filter oriented between air drawn in to said air sample tube and an IR sensor within said IR sensor module;
   (e) an analog to digital converter (ADC) electrically interconnected with said IR sensor module;
   (f) a microprocessor (CPU) electrically interconnected with said ADC and adapted for performing an algorithm that triggers detection of a gas when a change in IR energy between said IR emitter module and said IR sensor module is more rapid than a thermal drift of said IR sensor module; and
   (g) a battery power supply electrically interconnected with said CPU, said ADC, said air pump, said IR emitter module, and said IR sensor module.

2. The detector of claim 1 wherein said length is greater than said width and said width is greater than said thickness, wherein said intake probe tube is flexible and includes a moisture filter, and wherein said air pump draws air at a rate of approximately 100 cc/minute.

3. The detector of claim 1 wherein said optical bench comprises just one optical filter consisting of said wide band optical filter, said wide band optical filter allowing passage of IR wavelengths within the range of approximately 0.4 um to approximately 20 um and attenuating IR wavelengths outside of that range.

4. The detector of claim 1 wherein said optical bench comprises just two optical filters consisting of said wide band optical filter, said wide band optical filter allowing passage of IR wavelengths within the range of approximately 0.4 um to approximately 20 um and attenuating IR wavelengths outside of that range, and a second wide band optical filter positioned between air drawn in to said air sample tube and the IR emitter in said IR emitter module, said second wide band optical filter allowing passage of IR wavelengths within the range of approximately 0.4 um to approximately 20 um and attenuating IR wavelengths outside of that range.

5. The detector of claim 1 wherein said optical bench comprises just three optical filters consisting of said wide band optical filter as a first optical filter, said first optical filter allowing passage of IR wavelengths within the range of approximately 0.4 um to approximately 20 um and attenuating IR wavelengths outside of that range, and a second optical filter positioned between air drawn in to said air sample tube and the IR emitter in said IR emitter module, said second optical filter allowing passage of IR wavelengths within the range of approximately 0.4 um to approximately 20 um and attenuating IR wavelengths outside of that range, and a third optical filter positioned between air drawn in to said air sample tube and said first optical filter, said third optical filter allowing passage of a narrow band of IR wavelengths to detect a specific gas and attenuating IR wavelengths outside of that range.

6. The detector of claim 1 further comprising a speaker that provides a three tone idle signal every two seconds when not indicating detection of a target gas and that provides a high pitch squeal when indicating detection of said target gas, with the frequency of the squeal increasing with detection of increased concentration of said target gas, a visual display that provides a light when indicating detection of said target gas, with an increase in an amount of said light with detection of increased concentration of said target gas, and a tactile indication that provides a vibration with detection of said target gas, with an increase in vibration intensity with detection of increased concentration of said target gas.

7. The detector of claim 1 wherein said optical bench is insulated from bending by using a floating mounting of said bench whereby a space within which said bench is disposed is floatably secured within said housing such that distortions to said housing do not transfer to distortions of said space.

8. The detector of claim 1 wherein said optical bench is insulated from bending by being molded into molded structure comprising said housing enclosure.

9. A single-hand operable, single-hand sized, handheld portable gas leak detector comprising:
   (a) a single-hand sized housing enclosure having an interior volume and having a length, a width, and a thickness, the length extending longitudinally from a bottom surface to a top surface, the width extending from a left side surface to a right side surface, and the thickness extending from a back side surface to a front side surface, wherein said length is greater than said width and said width is greater than said thickness;
   (b) an intake probe tube extending away from the interior of the housing enclosure, wherein said intake probe tube includes a moisture filter;
   (c) an optical bench disposed within said housing enclosure that includes an air sample tube having an infrared (IR) emitter module at one end of the air sample tube and an IR sensor module at the opposite end of the air sample tube, an inlet near said IR emitter module fluidly connected with said intake probe tube, and an outlet near said IR sensor module fluidly connected with an air pump within said housing enclosure via a flexible tube, said optical bench being insulated from bending within said housing enclosure, wherein said air pump draws air at a rate of approximately 100 cc/minute;
   (d) said IR sensor module having a wide band optical filter oriented between air drawn in to said air sample tube and an IR sensor within said IR sensor module;
   (e) an analog to digital converter (ADC) electrically interconnected with said IR sensor module;
   (f) a microprocessor (CPU) electrically interconnected with said ADC and adapted for performing an algorithm that triggers detection of a gas when a change in IR energy between said IR emitter module and said IR sensor module is more rapid than a thermal drift of said IR sensor module;

(g) a battery power supply electrically interconnected with said CPU, said ADC, said air pump, said IR emitter module, and said IR sensor module;

(h) a speaker that provides a three tone idle signal every two seconds when not indicating detection of a target gas and that provides a high pitch squeal when indicating detection of said target gas, with the frequency of the squeal increasing with detection of increased concentration of said target gas;

(i) a visual display that provides a light when indicating detection of said target gas, with an increase in an amount of said light with detection of increased concentration of said target gas; and (j) a tactile indication that provides a vibration with detection of said target gas, with an increase in vibration intensity with detection of increased concentration of said target gas.

10. The detector of claim 9 wherein said intake probe tube is flexible.

11. The detector of claim 9 wherein said intake probe tube is rigid.

12. The detector of claim 9 wherein said optical bench comprises just one optical filter consisting of said wide band optical filter, said wide band optical filter allowing passage of IR wavelengths within the range of approximately 0.4 um to approximately 20 um and attenuating IR wavelengths outside of that range.

13. The detector of claim 9 wherein said optical bench comprises just two optical filters consisting of said wide band optical filter, said wide band optical filter allowing passage of IR wavelengths within the range of approximately 0.4 um to approximately 20 um and attenuating IR wavelengths outside of that range, and a second wide band optical filter positioned between air drawn in to said air sample tube and the IR emitter in said IR emitter module, said second wide band optical filter allowing passage of IR wavelengths within the range of approximately 0.4 um to approximately 20 um and attenuating IR wavelengths outside of that range.

14. The detector of claim 9 wherein said optical bench comprises just three optical filters consisting of said wide band optical filter as a first optical filter, said first optical filter allowing passage of IR wavelengths within the range of approximately 0.4 um to approximately 20 um and attenuating IR wavelengths outside of that range, and a second optical filter positioned between air drawn in to said air sample tube and the IR emitter in said IR emitter module, said second optical filter allowing passage of IR wavelengths within the range of approximately 0.4 um to approximately 20 um and attenuating IR wavelengths outside of that range, and a third optical filter positioned between air drawn in to said air sample tube and said first optical filter, said third optical filter allowing passage of a narrow band of IR wavelengths to detect a specific gas and attenuating IR wavelengths outside of that range.

15. The detector of claim 9 wherein said optical bench is insulated from bending by using a floating mounting of said bench whereby a space within which said bench is disposed is floatably secured within said housing such that distortions to said housing do not transfer to distortions of said space.

16. The detector of claim 9 wherein said optical bench is insulated from bending by being molded into molded structure comprising said housing enclosure.

17. A single-hand operable, single-hand sized, handheld portable gas leak detector comprising:

(a) a single-hand sized housing enclosure having an interior volume and having a length, a width, and a thickness, the length extending longitudinally from a bottom surface to a top surface, the width extending from a left side surface to a right side surface, and the thickness extending from a back side surface to a front side surface;

(b) an intake probe tube extending away from the interior of the housing enclosure, wherein said intake probe tube includes a moisture filter;

(c) an optical bench disposed within said housing enclosure that includes an air sample tube having an infrared (IR) emitter module at one end of the air sample tube and an IR sensor module at the opposite end of the air sample tube, an inlet near said IR emitter module fluidly connected with said intake probe tube, and an outlet near said IR sensor module fluidly connected with an air pump within said housing enclosure via a flexible tube, said optical bench being insulated from bending within said housing enclosure;

(d) said IR sensor module having a wide band optical filter oriented between air drawn in to said air sample tube and an IR sensor within said IR sensor module;

(e) an analog to digital converter (ADC) electrically interconnected with said IR sensor module;

(f) a microprocessor (CPU) electrically interconnected with said ADC and adapted for performing an algorithm that triggers detection of a gas when a change in IR energy between said IR emitter module and said IR sensor module is more rapid than a thermal drift of said IR sensor module; and (g) a battery power supply electrically interconnected with said CPU, said ADC, said air pump, said IR emitter module, and said IR sensor module;

(h) a speaker that provides a three tone idle signal every two seconds when not indicating detection of a target gas and that provides a high pitch squeal when indicating detection of said target gas, with the frequency of the squeal increasing with detection of increased concentration of said target gas;

(i) a visual display that provides a light when indicating detection of said target gas, with an increase in an amount of said light with detection of increased concentration of said target gas; and (j) a tactile indication that provides a vibration with detection of said target gas, with an increase in vibration intensity with detection of increased concentration of said target gas, wherein said optical bench comprises just three optical filters consisting of said wide band optical filter as a first optical filter, said first optical filter allowing passage of IR wavelengths within the range of approximately 0.4 um to approximately 20 um and attenuating IR wavelengths outside of that range, and a second optical filter positioned between air drawn in to said air sample tube and the IR emitter in said IR emitter module, said second optical filter allowing passage of IR wavelengths within the range of approximately 0.4 um to approximately 20 um and attenuating IR wavelengths outside of that range, and a third optical filter positioned between air drawn in to said air sample tube and said first optical filter, said third optical filter allowing passage of a narrow band of IR wavelengths to detect a specific gas and attenuating IR wavelengths outside of that range.

18. The detector of claim 17 wherein said intake probe tube includes a moisture filter, and wherein said air pump draws air at a rate of approximately 100 cc/minute.

19. The detector of claim 17 wherein said optical bench is insulated from bending by using a floating mounting of said bench whereby a space within which said bench is disposed is floatably secured within said housing such that distortions to said housing do not transfer to distortions of said space.

20. The detector of claim 17 wherein said optical bench is insulated from bending by being molded into molded structure comprising said housing enclosure.

* * * * *